US 8,342,177 B2

(12) United States Patent
Porges

(10) Patent No.: US 8,342,177 B2
(45) Date of Patent: Jan. 1, 2013

(54) SPILL RESISTANT HUMIDIFIER FOR USE IN A BREATHING ASSISTANCE SYSTEM

(75) Inventor: Charles E. Porges, Orinda, CA (US)

(73) Assignee: Covidien LP, Mansfield, MA (US)

( * ) Notice: Subject to any disclaimer, the term of this patent is extended or adjusted under 35 U.S.C. 154(b) by 561 days.

(21) Appl. No.: 12/565,267

(22) Filed: Sep. 23, 2009

(65) Prior Publication Data

US 2010/0071692 A1    Mar. 25, 2010

Related U.S. Application Data

(60) Provisional application No. 61/099,766, filed on Sep. 24, 2008.

(51) Int. Cl.
*A61M 16/00* (2006.01)
*A61M 15/00* (2006.01)

(52) U.S. Cl. ......... 128/204.17; 128/200.24; 128/203.12; 128/203.17; 128/203.26; 128/203.27

(58) Field of Classification Search .......... 128/200.11–200.24, 203.12, 203.15, 128/203.16, 203.17, 203.25, 203.26, 203.27, 128/204.14, 204.17, 204.18, 204.21, 205.27–205.29; 239/338, 102.1, 102.2; 261/129, 154, DIG. 65; 122/4 A, 5.5, 7 B, 13.01, 13.3–19.2, 33, 122/487, DIG. 7

See application file for complete search history.

(56) References Cited

U.S. PATENT DOCUMENTS

| 1,981,765 | A | * | 11/1934 | Weiss | 392/335 |
| 2,164,881 | A | * | 7/1939 | Meyerson | 128/203.17 |
| 2,542,529 | A | * | 2/1951 | Hunt | 422/305 |
| 3,244,152 | A | * | 4/1966 | Mixon et al. | 122/4 R |
| 4,753,758 | A | * | 6/1988 | Miller | 261/139 |
| 6,024,694 | A | | 2/2000 | Goldberg et al. | 600/22 |
| 6,553,712 | B1 | * | 4/2003 | Majerowski et al. | 43/131 |
| 2009/0194106 | A1 | | 8/2009 | Smith et al. | 128/203.16 |
| 2010/0242961 | A1 | * | 9/2010 | Mougel et al. | 128/203.16 |
| 2011/0100363 | A1 | | 5/2011 | Barclay et al. | 128/203.26 |

FOREIGN PATENT DOCUMENTS

GB    2010097 A   *  6/1979

* cited by examiner

*Primary Examiner* — Annette Dixon

(57) ABSTRACT

An apparatus for providing humidification in a breathing assistance system may include a first container at least partially defining a first volume for housing an absorbent material, a second container at least partially defining a second volume for holding a liquid, and one or more fluid passageways for communicating the liquid from the second volume to the absorbent material in the first volume.

18 Claims, 3 Drawing Sheets

SPILL RESISTANT HUMIDIFIER FOR USE IN A BREATHING ASSISTANCE SYSTEM

RELATED APPLICATION

This application claims priority from U.S. Provisional Application No. 61/099,766 filed, Sep. 24, 2008, which is hereby incorporated by reference herein in its entirety.

TECHNICAL FIELD

The invention relates to humidifiers, e.g., spill resistant humidifiers for use in breathing assistance systems (e.g., ventilators or CPAP devices).

BACKGROUND

Humidification of inspired gas is a standard practice in the care of mechanically ventilated patients, particularly where the upper airway is bypassed. Humidification may prevent various conditions, e.g., hypothermia, inspissation of airway secretions, destruction of airway epithelium, and atelectasis.

Humidifiers can be passive or active. Passive humidifiers (e.g., a heat-and-moisture exchanger (HME), which may be referred to as an "artificial nose") may trap heat and humidity from the patient's exhaled gas and return some of the trapped heat and humidity to the patient during the subsequent inhalation. Active, or heated, humidifiers typically pass the inspired gas through or over a heated water bath to increase the heat and water vapor content of the inspired gas. An example of a prior art heated humidifier 2 is shown in FIG. 1.

A common problem with heated humidifiers is liquid spillage. If the humidifier is tilted (sometimes even at a relatively small angle), water may spill through or out of one or more openings or junctions in the humidifier container. For example, in the prior art configuration shown in FIG. 1, if humidifier 2 is tilted, water may spill through openings 4 and/or 5 and into gas delivery conduits 6 and/or 8, which may be undesirable. If water spills into conduit 8, the patient may aspirate the water, which may be undesirable. Spilled water may also damage electronics or other components of the humidifier or apparatus to which the humidifier is attached (e.g., a ventilator).

SUMMARY

In accordance with one embodiment of the present disclosure, an apparatus for providing humidification in a breathing assistance system may include a first container at least partially defining a first volume for housing an absorbent material, a second container at least partially defining a second volume for holding a liquid, and one or more fluid passageways for communicating the liquid from the second volume to the absorbent material in the first volume.

In accordance with another embodiment of the present disclosure, an apparatus for providing humidification in a breathing assistance system may include one or more first walls defining a first volume configured to hold a liquid, one or more second walls defining a second volume configured to hold the liquid, one or more fluid passageways communicatively coupling the first volume with the second volume, and a conduit communicatively coupling the first volume with the second volume. The conduit may be configured to automatically regulate the communication of the liquid from the second volume to the first volume via the one or more fluid passageways.

In accordance with another embodiment of the present disclosure, a regulation system for a humidifier for a breathing assistance system may include an absorbent material configured to store liquid to be evaporated for delivery toward a patient. The absorbent material may be configured to be positioned in a first volume defined by a first container, and to receive liquid from a second volume via one or more fluid passageways communicatively coupling the first volume with the second volume.

In accordance with another embodiment of the present disclosure, a method for providing humidification for a breathing assistance system is provided. A first volume communicatively coupled to a second volume housing an absorbent material is at least partially filled with a liquid such that a portion of the liquid flows from the first volume to the second volume and is absorbed by the absorbent material. Heat is applied to the second volume such that liquid in the absorbent material evaporates for delivery toward a patient. The evaporation of liquid from the absorbent material may cause additional liquid to flow from the first volume to the second volume for absorption by the absorbent material.

In accordance with another embodiment of the present disclosure, an apparatus for providing humidification in a breathing assistance system is provided. The apparatus may include first housing means defining a first volume for holding a liquid, second housing means defining a second volume for holding the liquid, fluid conducting means for communicating liquid from the second volume to the first volume, and liquid regulation means for automatically regulating the communication of the liquid from the second volume to the first volume via the one or more fluid passageways. The liquid regulation means may include a conduit communicatively coupling the first volume with the second volume.

BRIEF DESCRIPTION OF THE DRAWINGS

For a more complete understanding of the present invention, and the advantages thereof, reference may be made to the following description of exemplary embodiments, taken in conjunction with the accompanying drawings, in which.

DETAILED DESCRIPTION OF THE DRAWINGS

Selected embodiments of the disclosure may be understood by reference, in part, to FIGS. 2-6, wherein like numbers refer to same and like parts. The present disclosure relates generally to spill resistant humidifiers, e.g., for use in breathing assistance systems such as ventilators, CPAP devices, etc. A humidifier according to the present disclosure may include a container for holding an absorbent material (e.g., a sponge), a separate container for holding a liquid, and one or more passageways and/or conduits for regulating the flow of the liquid into the absorbent material. The liquid is heated and evaporates from the sponge into a gas flow being delivered to a patient. As the liquid evaporates from the sponge, the humidifier automatically regulates the flow of additional liquid into the absorbent material. The container for holding the liquid may be substantially sealed, and may cooperate with the absorbent material to resist leakage of the liquid from the humidifier, regardless of the orientation of the humidifier (e.g., the degree to which the humidifier is tipped).

Figure 1:
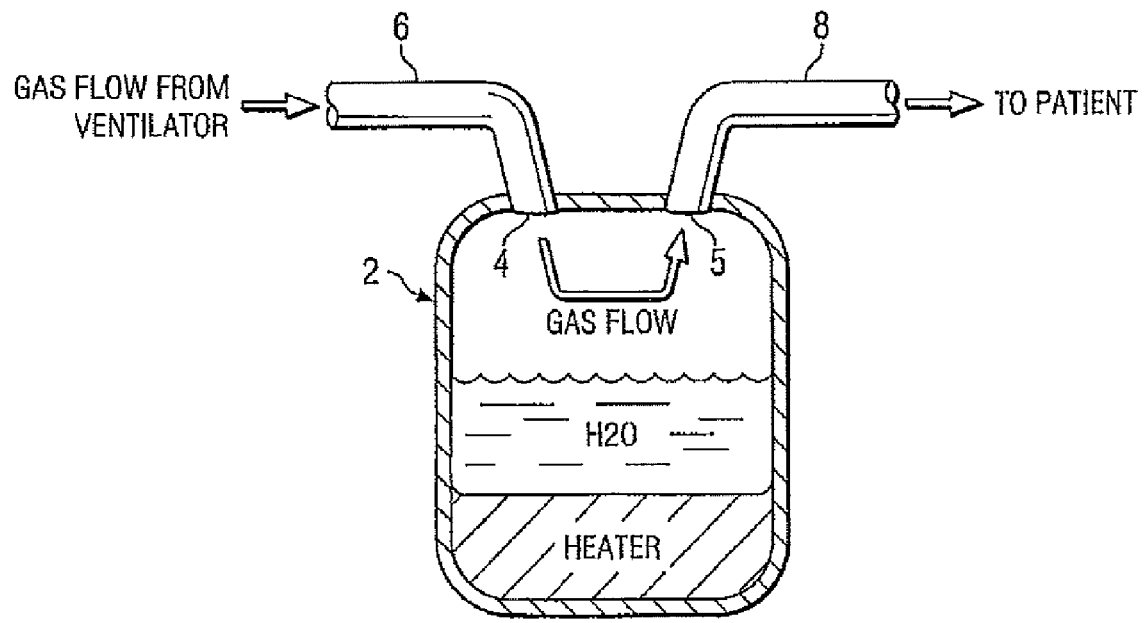
FIG. 1 illustrates an example prior art heated humidifier for use with a ventilator.
Figure 2:
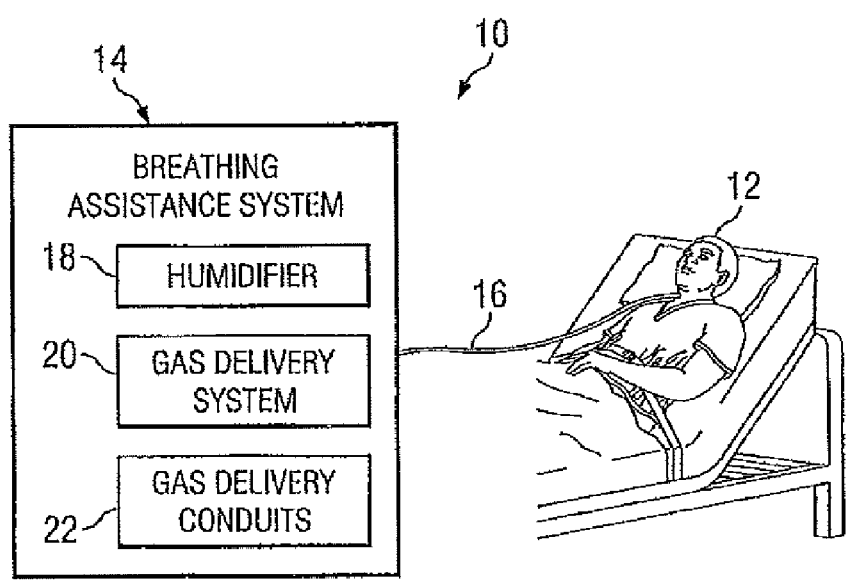
FIG. 2 illustrates an example breathing assistance system having a heated humidifier, according to one embodiment of the present disclosure.

FIG. 2 illustrates an example breathing assistance system 10, according to one embodiment of the disclosure. Breathing assistance system 10 may be generally configured to provide breathing assistance (e.g., providing ventilation and/or treating an apnea or other breathing condition) to a patient 12. Breathing assistance system 10 may include a breathing assistance apparatus 14, a connection system 16 for connecting breathing assistance apparatus 14 to patient 12, and a humidifier 18.

Breathing assistance apparatus 14 may comprise any device, apparatus, or system for delivering breathing gas to a patient, e.g., a ventilator, a respirator, a CPAP device, or a BiPAP device. Connection system 16 may be generally configured to deliver gas from breathing assistance apparatus 14 to patient 12 and/or to remove exhaust gas away from patient 12. For example, connection system 16 may comprise any suitable type of breathing circuit (e.g., a single-limb or dual-limb circuit) and/or a patient connection apparatus. A patient connection apparatus may include any device or devices configured to connect the breathing circuit to one or more breathing passageways of patient 12. For example, a patient connection apparatus may include a patient connection tube directly connected to the patient's trachea, an artificial airway (e.g., an endotracheal tube or other device) inserted in the patient's trachea, and/or a mask, cushion or nasal pillows positioned over the patient's nose and/or mouth.

Breathing assistance apparatus 14 may include a gas delivery system 20, one or more gas delivery conduits 22, and/or any other suitable components for providing breathing assistance to patient 12. For example, breathing assistance apparatus 14 may include one or more sensors for sensing, detecting, and/or monitoring one or more parameters related to system 10 and/or patient 12, a control system for controlling gas delivery system 20, various user interfaces, and a display.

Gas delivery system 20 may include any device or devices configured to generate, supply, and/or deliver gas (e.g., pressurized air) toward patient 12 via connection system 14. For example, gas delivery system 20 may comprise a device capable of generating pressurized air (e.g., a motorized blower or piston-based device), a wall outlet through which pressurized air may be supplied (e.g., in a hospital or clinic), valves configured to control the supply of gas to the patient (e.g., a PSOL or other solenoid valve), one or more tanks of compressed gas, a compressor, or any other suitable source of pressurized or non-pressurized gas.

As used herein, the term "gas" may refer to any one or more gases and/or vaporized substances suitable to be delivered to and/or from a patient via one or more breathing orifices (e.g., the nose and/or mouth), such as air, nitrogen, oxygen, any other component of air, $CO_2$, vaporized water, vaporized medicines, and/or any combination of two or more of the above, for example.

As used herein, the term "patient" may refer to any person or animal that may receive breathing assistance from system 10, regardless of the medical status, official patient status, physical location, or any other characteristic of the person. Thus, for example, patients may include persons under official medical care (e.g., hospital patients), persons not under official medical care, persons receiving care at a medical care facility, persons receiving home care, etc.

Humidifier 18 may be generally operable to humidify (e.g., to increase the heat and/or water vapor content) of gas to be delivered to a patient 12. Humidifier 18 may be an active, or heated, humidifier. In some embodiments, humidifier 18 may be integrated with, connected to, or otherwise associated with breathing assistance apparatus 14. For example, humidifier 18 may be permanently or removably attachable to breathing assistance apparatus 14. In some embodiments, humidifier 18 may be communicatively coupled (permanently or removably) to one or more gas delivery conduits 22 such that humidifier 18 may humidify gas being delivered to patient 12 via such one or more gas delivery conduits 22. Humidifier 18 may be coupled to a gas delivery conduit 22 in any suitable manner.

In other embodiments, humidifier 18 may not be associated with a breathing assistance apparatus 14. For example, humidifier 18 may be used as a stand-alone humidifier (e.g., to provide humidified air to a patient) or in association with any other system using humidified gasses.

Figure 3:
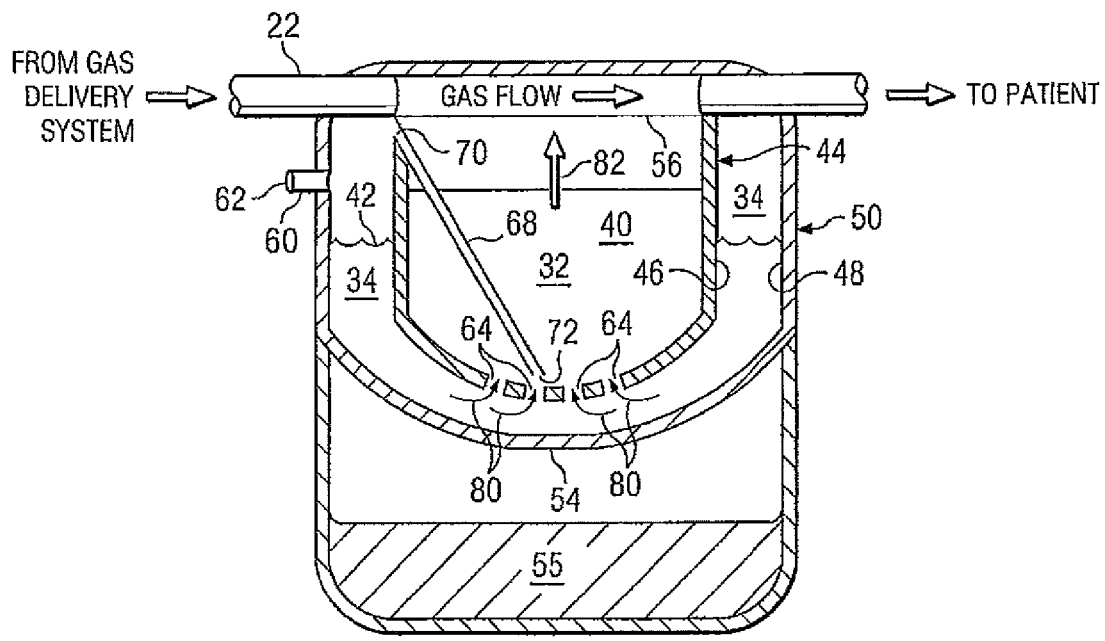
FIG. 3 illustrates an example humidifier for use in a breathing assistance system 10, according to one embodiment of the present disclosure.

FIG. 3 illustrates an example humidifier 18 for use in a breathing assistance system 10, according to one embodiment of the present disclosure. Humidifier 18 may be connected (permanently or removably) to gas delivery conduit 22 used to deliver gas toward patient 12. In other embodiments, humidifier 18 may be connected (permanently or removably) to connection system 16, may be otherwise associated with system 10, or may not be associated with system 10 (e.g., a stand-alone humidifier).

As shown in FIG. 3, humidifier 18 may define a first volume 32 and a second volume 34. First volume 32 may house an absorbent material 40 configured to absorb a liquid 42 received from second volume 34 (as discussed below) and, when heated, to communicate the liquid 42 upward towards gas delivery conduit 22 for vaporization/evaporation, as indicated by arrow 82. Absorbent material 40 may include any suitable material or materials operable to absorb liquid 42, e.g., sponges; fluid-absorbing fibers such as cellulose from wood pulp, cotton fibers, or coated synthetic fibers; absorbent foam; porous materials; and fibrous materials. Absorbent material 40 may include multiple layers of one or multiply types of absorbent materials. Absorbent material 40 may include one or more fins or similar features to increase the surface area of absorbent material 40, which may improve the performance of absorbent material 40.

In some embodiments, absorbent material 40 is permanently attached to or housed in first volume 32. In other embodiments, absorbent material 40 is removably attached to or housed in first volume 32, such that absorbent material 40 may be removed and/or replaced, e.g., for cleaning, disinfecting, sterilizing, drying, replacing, or for any other reason. In some embodiments, absorbent material 40 may be replaced after use by each patient, e.g., to prevent cross-patient bacterial contamination. In addition, absorbent material 40 may be cleaned or replaced during long term use by a single patient.

Second volume 34 may be configured to house liquid 42 for delivery to absorbent material 40. Liquid 42 may include any one or more liquids suitable to be vaporized into a gas flow for delivery to patient 12, e.g., water, another medically useful liquid, or any other suitable liquid. Second volume 34 may be substantially sealed (except for openings 64 discussed below) to prevent liquid 42 from leaking from second volume 34 into gas delivery conduit 22 or otherwise leaking out of humidifier 18.

In some embodiments, first volume 32 may be defined at least partially by a first container and second volume 34 may be defined at least partially by a second container. In the embodiment shown in FIG. 3, first volume 32 is defined in part by a first container 44 and second volume 34 is defined generally between an outer wall 46 of first container 44 and an inner wall 48 of a second container 50. In this embodiment, first container 44 is positioned at least partially within or surrounded by second container 50, and thus, first volume 32 is located at least partially within or surrounded by second volume 34. In other embodiments, second container 50 is positioned at least partially within or surrounded by first container 44, and thus, second volume 34 is located at least partially within or surrounded by first volume 32. For example, in such embodiments, a ring-shaped absorbent material 40 housed in first container 44 may at least partially surround liquid 42 held in second container 50. In still other embodiments, neither first volume 32 nor second volume 34 may be located within or surrounded by the other. For example, first volume 32 and second volume 34 may be located side-by-side, or one on top of the other.

First container 44 and second container 50 may have any suitable shape and/or configuration. In the embodiment shown in FIG. 3, first and second containers 44 and 50 have a cylindrical upper portion and a curved or sloped bottom portion. In this embodiment, second container 50 has a substantially flat bottom plate 54. Flat bottom plate 54 may have any size, and in some embodiments, may extend completely across the width of second container 50. In other embodiments, second container 50 may be curved at its bottom point. In other embodiments, first container 44 and/or second container 50 may have a U-shaped cross-section, a U-shaped cross-section with a flat bottom, a V-shaped cross-section, a cylindrical shape, a rectangular shape, a spherical shape, a tapered shape, or any other suitable shape.

In some embodiments, first container 44 and/or second container 50 may be shaped or configured to conduct and/or dissipate heat received from a heater 55 as desired. Heater 55 may include any system or device for providing heat to fluid 42 such that fluid 42 in absorbent material 40 evaporates into the gas flow through gas delivery conduit 22, as indicated by arrow 82. For example, heater 55 may include an electrical, gas, or battery-powered heating device.

First container 44 and second container 50 may be formed from any suitable material or materials. In some embodiments, first container 44 and/or second container 50 may be formed from one or more heat conductive materials (e.g., metal) in order to promote the conduction of heat from heater 55.

First container 44 may define one or more openings 56 communicatively coupled to gas delivery conduit 22 such that liquid 42 from absorbent material 40 may evaporate into the gas flow in gas delivery conduit 22. Each opening 56 may have any suitable shape and/or configuration.

Second container 50 may include a port 60 for adding fluid 42 into second volume 34. Port 60 may be configured and/or located to prevent or hinder overfilling of second container 50. In other embodiments, port 60 may be located near the bottom of the container 50 such that a user may invert container 50 to fill humidifier 18. A sealing device (e.g., a screw cap) 62 may be removably connected to port 60 to provide a leak-free seal.

One or more fluid passageways 64 may be formed for communicating liquid 42 from second volume 34 to first volume 32. In the illustrated embodiment, fluid passageways 64 comprise openings formed in a bottom portion of first container 44. Such openings 64 allow liquid 42 from second volume 34 to flow into first volume 32, where liquid 42 may be absorbed by absorbent material 40.

One or more conduits 68 may communicatively couple first volume 32 with second volume 34 to regulate the flow of liquid 42 from second volume 34 to first volume 32 via fluid passageways 64. Each conduit 68 may have any suitable shape and/or configuration, and may be formed from any suitable material. For example, a conduit 68 may be formed from a flexible material (e.g., plastic), a rigid material (e.g., metal), or any other suitable material. Each conduit 68 may extend in any suitable direction(s) and may be positioned in any suitable position. In the illustrated embodiment, a conduit 68 extends from a first end 70 opening into second volume 34 to a second end 72 opening near the bottom of first container 44.

First end 70 of conduit 68 may be located above second end 72 when humidifier 18 is in an upright position. In some embodiments, first end 70 opens into second volume 34 at a location above port 60 to ensure that liquid 42 does not flow down conduit 68. Second end 72 of conduit 68 may be located in or proximate absorbent material 40. For example, in the embodiment shown in FIG. 3, second end 72 opens at a location near the bottom of absorbent material 40. At least a portion of the length of conduit 68 may be partially or completely surrounded by absorbent material 40. Thus, absorbent material 40 may have an opening or cutout to receive conduit 68. In other embodiments, conduit 68 may not substantially extend through first volume 32, such that absorbent material 40 need not include a significant opening or cutout to receive conduit 68. For example, conduit 68 may extend along the inside or outside of the wall of container 44 and may extend into first volume 32 near the bottom of first volume 32. Thus, absorbent material 40 may include a relatively small opening or cutout (or no opening or cutout) to receive conduit 68.

Conduit 68 may regulate the flow of liquid 42 from second volume 34 to first volume 32 via fluid passageways 64 in the following manner. When container 50 is filled with liquid 42 (via port 60), a portion of the liquid 42 flows through fluid passageways 64 and is absorbed by absorbent material 40, as indicated by arrows 80. When absorbent material 40 is saturated to a particular level or amount, second end 72 of conduit 68 may be sealed by liquid 42, which prevents air from flowing upward through conduit 68, which creates a sealed volume of air in second volume 34 above liquid 42, which restricts additional liquid 42 from flowing through fluid passages 64.

As the liquid 42 in absorbent material 40 is heated, rises, and evaporates into the gas flow in gas delivery conduit 22, as indicated by arrow 82, the portion of absorbent material 40 near second end 72 of conduit 68 progressively dries out until second end 72 is no longer sealed by liquid 42. Once second end 72 is no longer sealed by liquid 42, air in first volume 32 flows upward through conduit 68 (i.e., toward first end 70), thus allowing additional liquid 42 to flow from second volume 34 through fluid passages 64 and into absorbent material 40, as indicated by arrows 80, until second end 72 of conduit 68 once again becomes sealed. This process may repeat any number of times. In this manner, conduit 68 may automatically regulate the flow of liquid 42 within humidifier 18.

It should be understood that direction-related terms such as "bottom" and "upward," for example, used above regarding FIG. 3 are intended to refer to the particular orientation of humidifier 18 shown in FIG. 3, and are not intended to be limiting.

Figure 4:
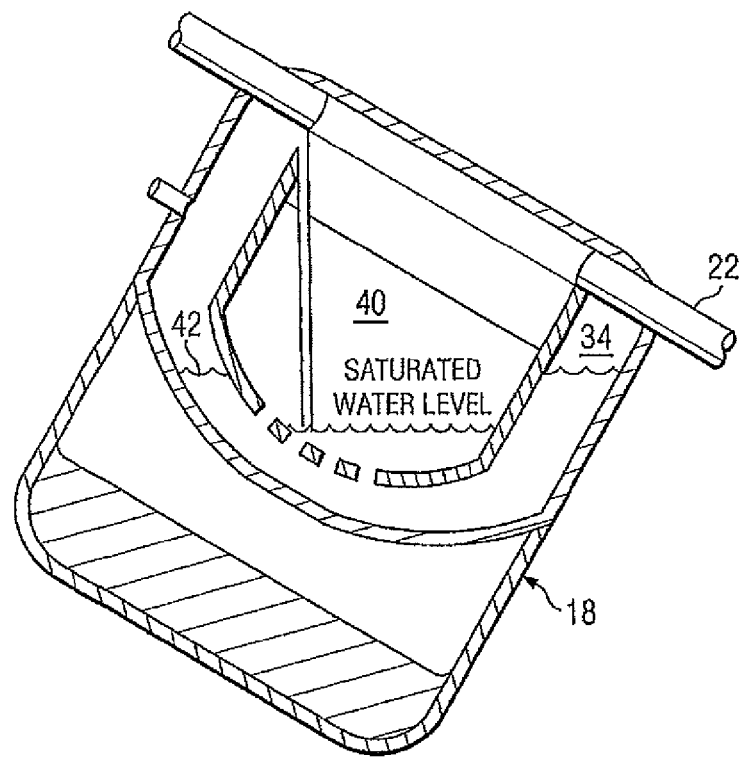
FIG. 4 illustrates the example humidifier of FIG. 3 tilted approximately 30 degrees from its normal orientation, according to one embodiment of the present disclosure.
Figure 5:
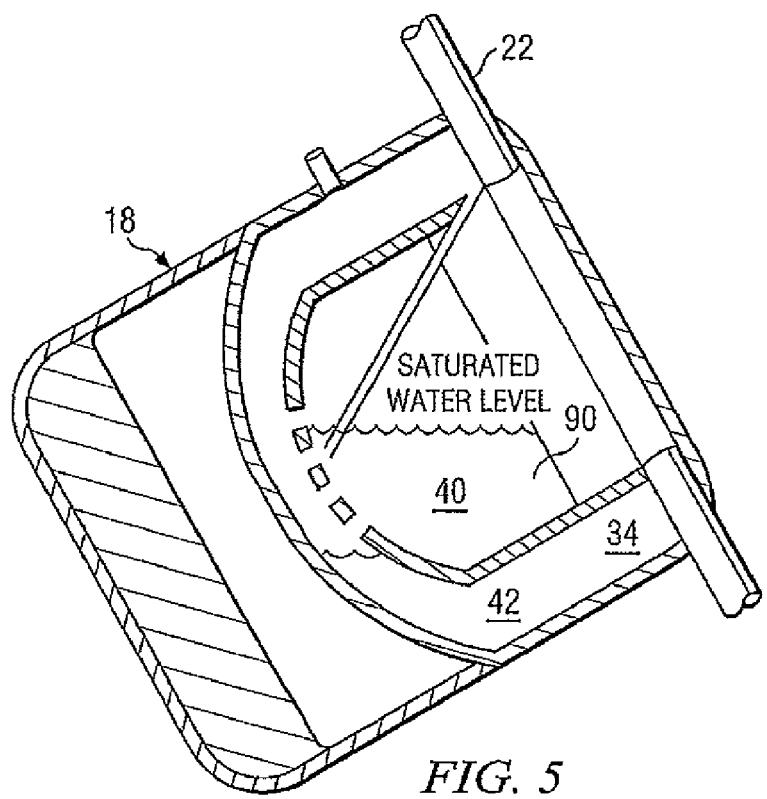
FIG. 5 illustrates the example humidifier of FIG. 3 tilted approximately 60 degrees from its normal orientation, according to one embodiment of the present disclosure.

In some embodiments, humidifier 18 is substantially spill-resistant such that liquid 42 is substantially prevented from leaking out of humidifier 18 (e.g., into gas delivery conduit 22 or otherwise out of humidifier 18), regardless of the orientation of the humidifier 18, e.g., as shown in FIGS. 4 and 5.

FIG. 4 illustrates an example humidifier 18 tilted approximately 30 degrees from its normal upright orientation, according to one embodiment of the present disclosure. When humidifier 18 is tilted as shown, liquid 42 may shift toward one side of second volume 34, and a portion of liquid 42 may flow into absorbent material 40. In such orientation, liquid 42 is substantially prevented from leaking from humidifier 18.

FIG. 5 illustrates an example humidifier 18 tilted approximately 60 degrees from its normal upright orientation, according to one embodiment of the present disclosure. When humidifier 18 is tilted as shown, liquid 42 may shift toward one side of second volume 34, and a portion of liquid 42 may flow into absorbent material 40. A top portion 90 of absorbent material 40 may become moist or partially saturated, but may resist leakage of liquid 42 into gas delivery conduit 22. Thus, in such orientation, liquid 42 may be substantially prevented from leaking from humidifier 18.

Figure 6:
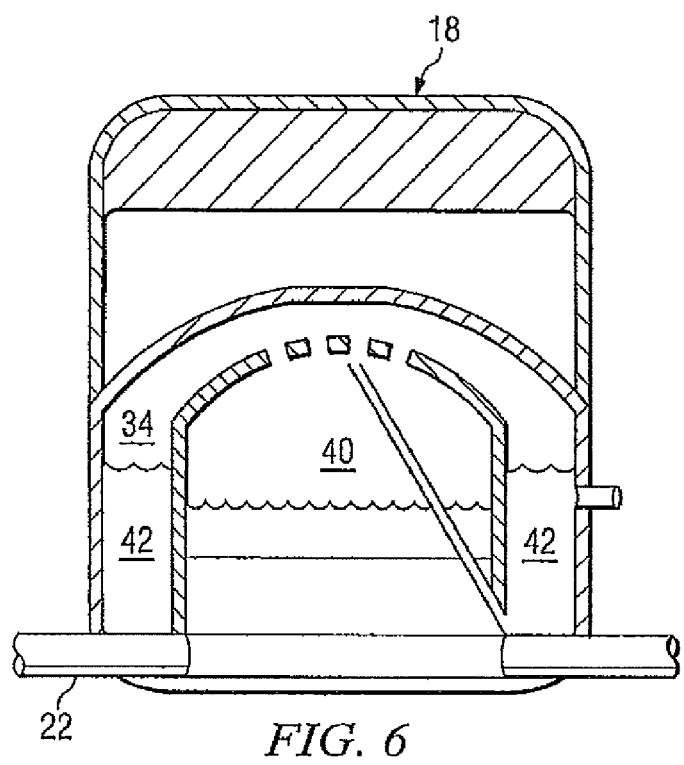
FIG. 6 illustrates the example humidifier of FIG. 3 tilted approximately 180 degrees from its normal orientation, according to one embodiment of the present disclosure.

FIG. 6 illustrates an example humidifier 18 tilted approximately 180 degrees from its normal upright orientation, according to one embodiment of the present disclosure. When humidifier 18 is oriented as shown, liquid 42 may flow into a top portion of second volume 34, which is sealed from leakage. As humidifier 18 is tilted into this orientation, a portion of liquid 42 may flow into absorbent material 40 via fluid passageways 64. Portions of absorbent material 40 may become moist or partially saturated, but may resist leakage of liquid 42 into gas delivery conduit 22. Thus, in such orientation, liquid 42 may be substantially prevented from leaking from humidifier 18.

It will be appreciated that while the disclosure is particularly described in the context of breathing assistance systems, the apparatuses, techniques, and methods disclosed herein may be similarly applied in other contexts. Additionally, it should be understood that various changes, substitutions and alterations can be made herein without departing from the spirit and scope of the disclosure as illustrated by the following claims.

What is claimed is:

1. An apparatus for providing humidification in a breathing assistance system, the apparatus comprising:
    a first container at least partially defining a first volume for housing an absorbent material;
    a second container at least partially defining a second volume for holding a liquid;
    one or more fluid passageways for communicating the liquid from the second volume to the absorbent material in the first volume; and
    a conduit communicatively coupling the first volume with the second volume and distinct from the one or more fluid passageways for communicating the liquid from the second volume to the absorbent material in the first volume, the conduit configured such that:
        when a first end of the conduit is not sealed by liquid in the first volume, the conduit is operable to communicate gas from the first volume to the second volume to facilitate communication of the liquid from the second volume to the first volume via the one or more fluid passageways; and
        when the first end of the conduit is sealed by liquid in the first volume, the conduit is not operable to communicate gas from the first volume to the second volume to facilitate communication of the liquid from the second volume to the first volume via the one or more fluid passageways.

2. An apparatus according to claim 1, wherein the first and second containers are configured to substantially prevent leakage of the liquid from the apparatus regardless of the orientation of the apparatus.

3. An apparatus according to claim 1, wherein the one or more fluid passageways comprise openings formed in a bottom portion of the first container.

4. An apparatus according to claim 1, wherein the first container is positioned at least partially within the second container.

5. An apparatus according to claim 1, wherein the second container is positioned at least partially within the first container.

6. An apparatus according to claim 1, wherein;
    the first container has a first wall;
    the second container has a second wall; and
    the second volume is at least partially defined by the first and second walls.

7. An apparatus according to claim 1, wherein the first container includes an opening communicatively coupled to a gas delivery conduit, the opening of the first container configured for communicating evaporated liquid from the absorbent material to gas delivery conduit.

8. An apparatus according to claim 1, wherein the conduit extends from a location proximate a top portion of the first container to a location proximate a bottom portion of the first container.

9. An apparatus according to claim 1, wherein a first end of the conduit is located in the absorbent material.

10. An apparatus for providing humidification in a breathing assistance system, the apparatus comprising:
    one or more first walls defining a first volume configured to hold a liquid;
    one or more second walls defining a second volume configured to hold the liquid;
    one or more fluid passageways communicatively coupling the first volume with the second volume; and
    a conduit communicatively coupling the first volume with the second volume and distinct from the one or more fluid passageways communicatively coupling the first volume with the second volume, the conduit configured to automatically regulate the communication of the liquid from the second volume to the first volume via the one or more fluid passageways by:
        allowing gas flow from the first volume to the second volume when a first end of the conduit is not sealed by liquid in the first volume, thereby facilitating communication of the liquid from the second volume to the first volume via the one or more fluid passageways; and
        preventing gas flow from the first volume to the second volume when the first end of the conduit is sealed by liquid in the first volume, thereby resisting communication of the liquid from the second volume to the first volume via the one or more fluid passageways.

11. An apparatus according to claim 10, wherein the conduit extends from a location proximate a top portion of the second volume to a location proximate a bottom portion of the first volume.

12. An apparatus according to claim 10, wherein:
    the first volume is configured to hold an absorbent material; and
    a first end of the conduit is located in the absorbent material.

13. A regulation system for a humidifier for a breathing assistance system, the regulation system comprising:
- a first volume defined by a first container;
- a second volume;
- one or more fluid passageways communicatively coupling the first volume with the second volume;
- an absorbent material positioned in the first volume and configured to receive liquid from a second volume via one or more fluid passageways communicatively coupling the first volume with the second volume and to store the liquid to be evaporated for delivery toward a patient; and
- a flow regulation conduit distinct from the one or more fluid passageways and including a first end positioned in the absorbent material, the first end of the flow regulation conduit configured to switch between an unblocked state and a blocked state based on an amount of liquid in the second volume;
- wherein fluid flow from the second volume to the first volume via the one or more fluid passageways is regulated based at least on the unblocked state or blocked state of the first end of the flow regulation conduit.

14. A regulation system according to claim 13, wherein the absorbent material is removable from the regulation system.

15. A regulation system according to claim 13, wherein the absorbent material is configured to receive heat causing liquid in the absorbent material to evaporate for mixing with gas being delivered to the patient.

16. A method for providing humidification for a breathing assistance system, the method comprising:
- at least partially filling a first volume with a liquid, the first volume communicatively coupled to a second volume housing an absorbent material such that a portion of the liquid in liquid form, flows from the first volume to the second volume and is absorbed by the absorbent material; and
- applying heat to the second volume such that liquid in the absorbent material evaporates for delivery toward a patient, wherein additional liquid flow from the first volume to the second volume for absorption by the absorbent material results at least in part due to the evaporation of the liquid from the absorbent material.

17. A method according to claim 16, wherein evaporation of liquid from the absorbent material causes a conduit to become unsealed and to communicate gas from the first volume to the second volume, which facilitates the additional liquid flow from the first volume to the second volume for absorption by the absorbent material.

18. An apparatus for providing humidification in a breathing assistance system, the apparatus comprising:
- first means for holding a liquid and defining a first volume;
- second means for holding the liquid and defining a second volume;
- fluid conducting means for communicating liquid from the second volume to the first volume; and
- liquid regulation means for automatically regulating the communication of the liquid from the second volume to the first volume via the fluid conducting means, the liquid regulation means including a conduit communicatively coupling the first volume with the second volume and distinct from the fluid conducting means for communicating liquid from the second volume to the first volume, the conduit configured such that:
  - when a first end of the conduit is not sealed by liquid in the first volume, the conduit is operable to communicate gas from the first volume to the second volume to facilitate communication of the liquid from the second volume to the first volume via the fluid conducting means; and
  - when the first end of the conduit is sealed by liquid in the first volume, the conduit is not operable to communicate gas from the first volume to the second volume to facilitate communication of the liquid from the second volume to the first volume via the fluid conducting means.

* * * * *